United States Patent
Chen et al.

(10) Patent No.: US 11,578,041 B2
(45) Date of Patent: Feb. 14, 2023

(54) CRYSTALS OF HYDROXYCHLOROQUINE SULFATE

(71) Applicant: Genovate Biotechnology Co. Ltd., Hsin-Chu (TW)

(72) Inventors: Jen Chen, Hsin-Chu (TW); Nai-tung Yao, Hsin-Chu (TW)

(73) Assignee: Genovate Biotechnology Co. Ltd., Hsin-Chu (TW)

( * ) Notice: Subject to any disclaimer, the term of this patent is extended or adjusted under 35 U.S.C. 154(b) by 147 days.

(21) Appl. No.: 17/139,135

(22) Filed: Dec. 31, 2020

(65) Prior Publication Data

US 2021/0323925 A1 Oct. 21, 2021

Related U.S. Application Data

(60) Provisional application No. 63/013,219, filed on Apr. 21, 2020.

(51) Int. Cl.
*C07D 215/46* (2006.01)

(52) U.S. Cl.
CPC ........ *C07D 215/46* (2013.01); *C07B 2200/13* (2013.01)

(58) Field of Classification Search
CPC .......................... C07D 215/46; C07B 2200/13
See application file for complete search history.

(56) References Cited

U.S. PATENT DOCUMENTS 2,546,658 A * 3/1951 Alexanderr .......... C07D 215/46
546/163
5,314,894 A * 5/1994 Stecher ................ C07D 215/46
546/163

FOREIGN PATENT DOCUMENTS

EP 0588430 A1 3/1994

OTHER PUBLICATIONS

Blaney et al "A Practical Synthesis of the Enantiomers of Hydroxychloroquine" Tetrahedron: Asymmetry vol. 5, pp. 1815-1822, 1994.
Caira "Crystalline Polymorphism of Organic Compounds" Topics in Current Chemistry vol. 198, pp. 163-208, 1998.

* cited by examiner

*Primary Examiner* — Timothy R Rozof
(74) *Attorney, Agent, or Firm* — Cesari & McKenna, LLP

(57) ABSTRACT

Two crystals of (S)-(+)-hydroxychloroquine sulfate. One crystal features diffraction peaks at 12.3±0.1°, 13.1±0.1°, 17.9±0.1°, 22.8±0.1°, 23.4±0.1°, 25.1±0.1°, and 26.3±0.1° as 2θ angles in a powder X-ray diffraction pattern. The other crystal features diffraction peaks at 12.8±0.1°, 14.5±0.1°, 16.7±0.1°, 17.6±0.1°, 20.2±0.1°, 21.4±0.1°, 23.8±0.1°, 25.7±0.1°, and 26.0±0.1° as 2θ angles in a powder X-ray diffraction pattern. Also disclosed are methods of preparing crystals of (S)-(+)-hydroxychloroquine sulfate.

18 Claims, 5 Drawing Sheets

FIG. 1 A PXRD pattern of a first crystal of (S)-(+)-hydroxychloroquine sulfate ("type A crystal") as 2θ angles
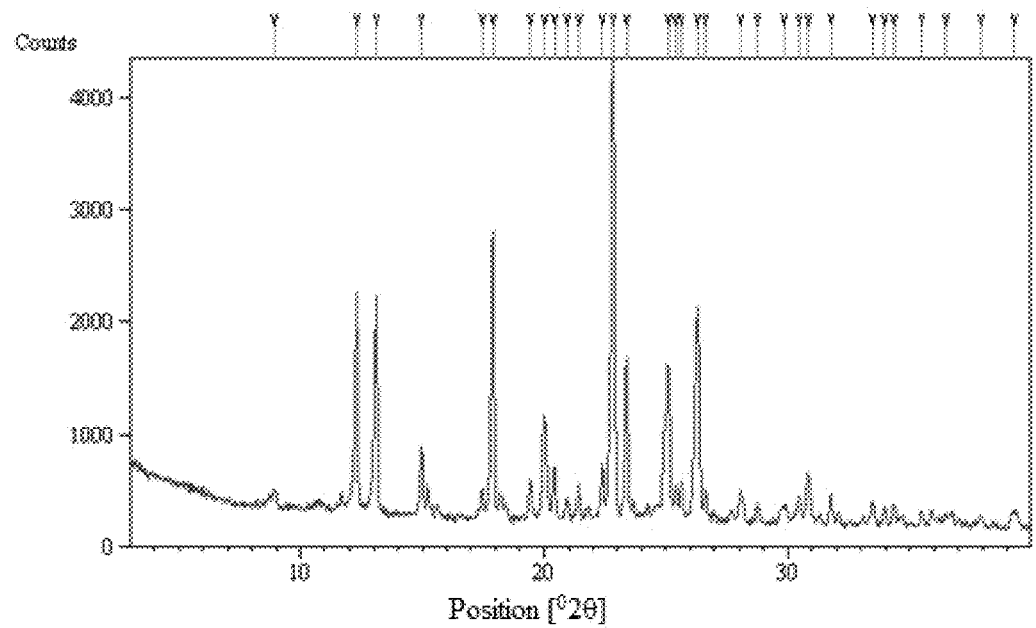
FIG. 2 A differential scanning calorimetry curve of type A crystal
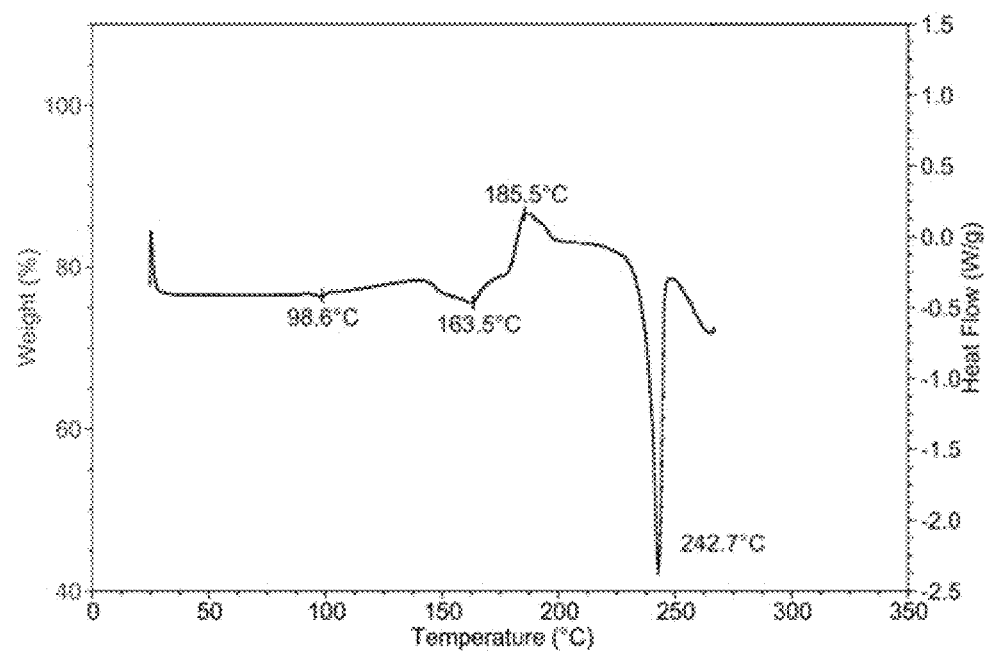

FIG. 3  A PXRD pattern of a second crystal of (S)-(+)-hydroxychloroquine sulfate ("type B crystal") as 2θ angles
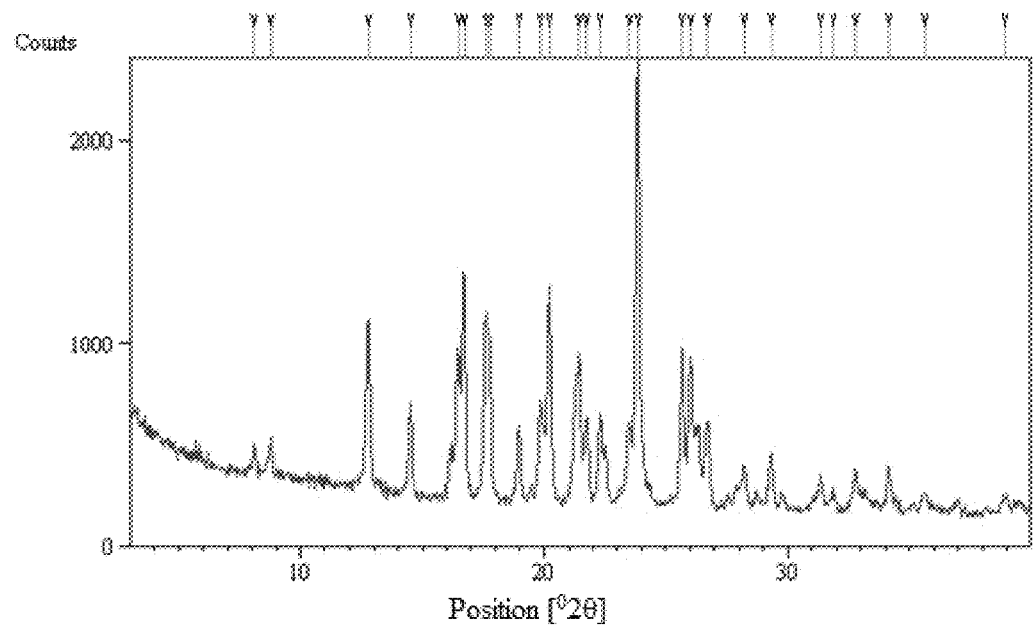
FIG. 4  A differential scanning calorimetry curve of type B crystal
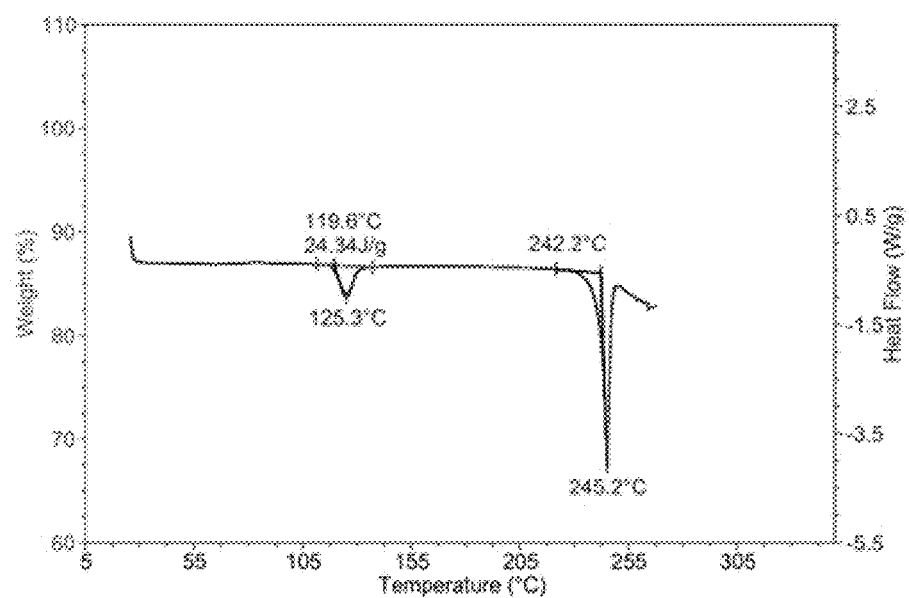

FIG. 5  A PXRD pattern of a third crystal of (S)-(+)-hydroxychloroquine sulfate ("type C crystal") as 2θ angles
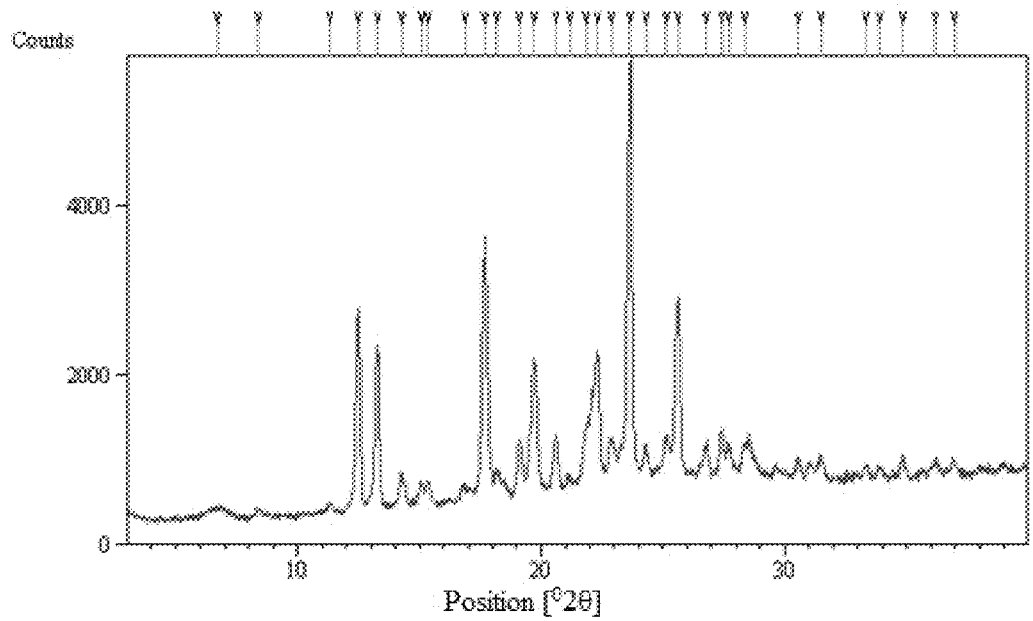
FIG. 6  A PXRD pattern of a fourth crystal of (S)-(+)-hydroxychloroquine sulfate ("type D crystal") as 2θ angles
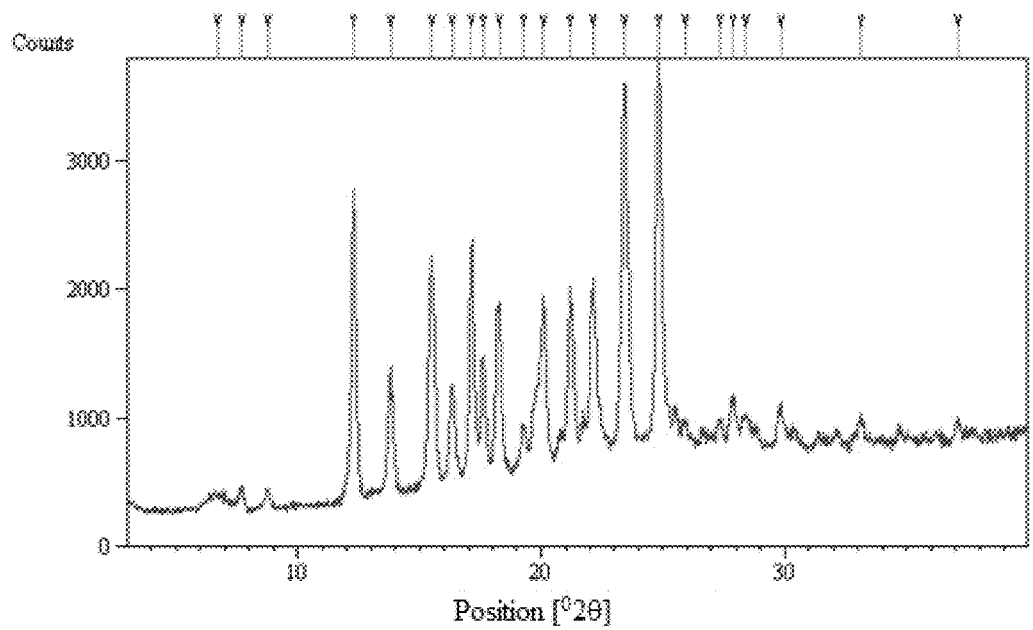

FIG. 7 Moisture adsorption and desorption curves of type A crystal
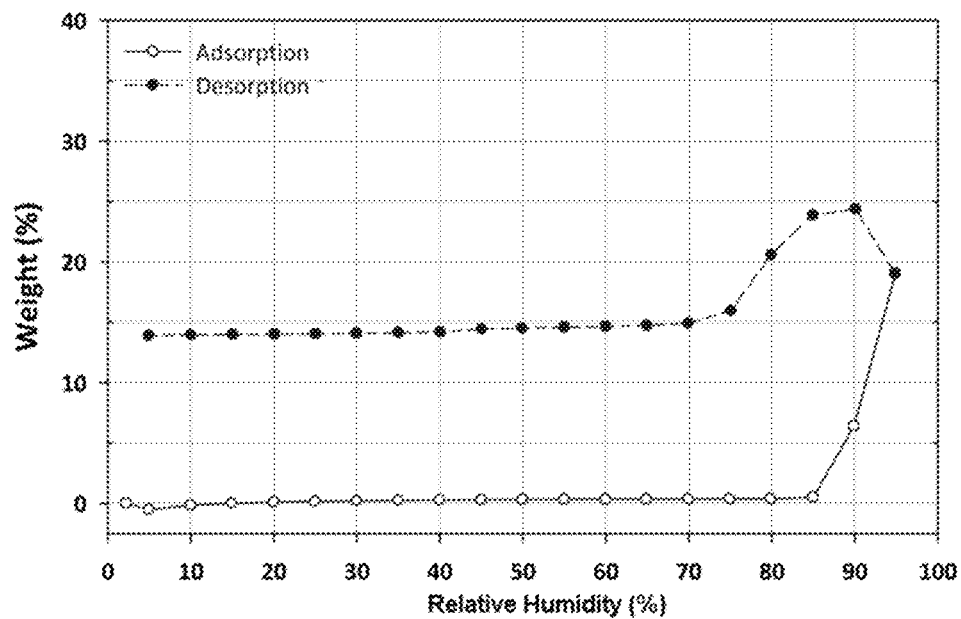
FIG. 8 Moisture adsorption and desorption curves of type B crystal
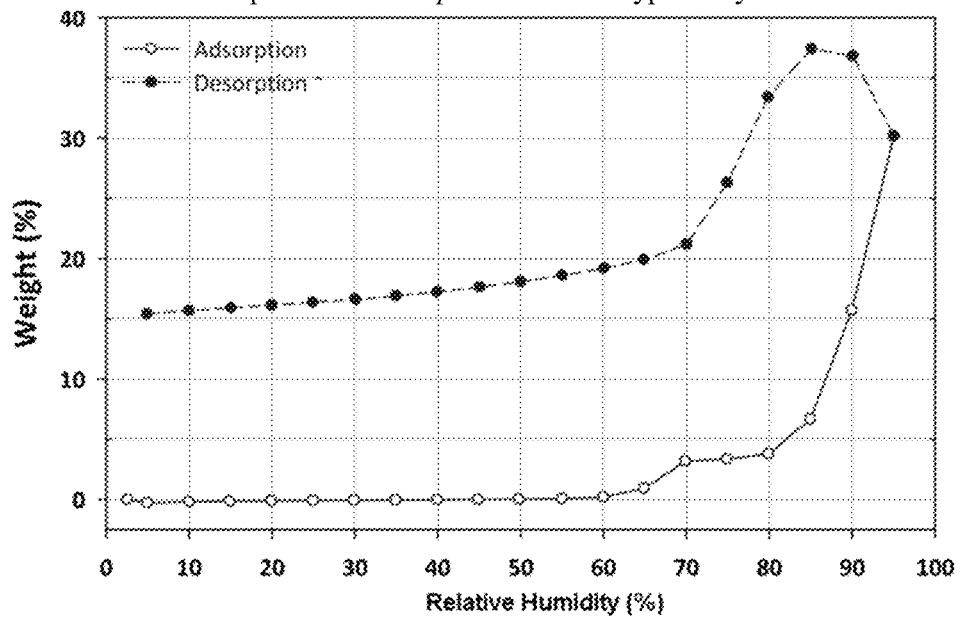

FIG. 9 Moisture adsorption and desorption curves of an amorphous form of (S)-(+)-hydroxychloroquine sulfate
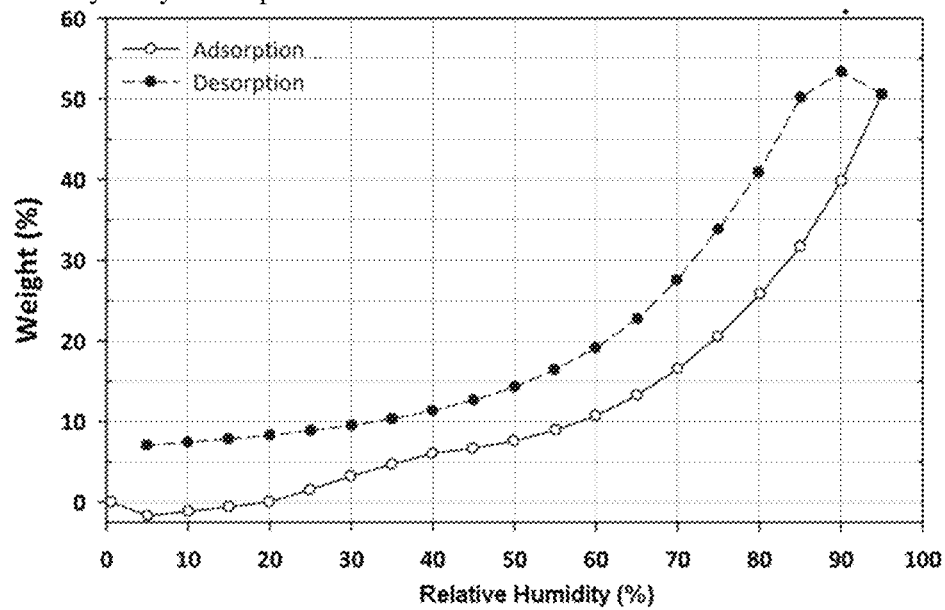

US 11,578,041 B2

CRYSTALS OF HYDROXYCHLOROQUINE SULFATE

CROSS-REFERENCE TO RELATED APPLICATIONS

The present application claims the benefit of U.S. Provisional Patent Application Ser. No. 63/013,219, filed on Apr. 21, 2020. The content of this prior application is hereby incorporated by reference in its entirety.

BACKGROUND (±)-Hydroxychloroquine sulfate is one of the essential drugs in the World Health Organization Model List for treating, among other, discoid and systemic lupus erythematosus, chronic polymorphous solar eruption, chronic rheumatoid arthritis, and malaria caused by *Plasmodium falciparum* and *Plasmodium vivax*.

The drug has two optical isomers, i.e., the (R)-(−)-isomer and the (S)-(+) isomer. It is administered to a patient as a racemic (50:50) mixture of these two isomers. Long-term and high-dosage administration can damage retinas and lead to vision impairments in some patients, due to drug accumulation in ocular tissues.

An animal study using the Rat Pleurisy Macrophage Model shows that the (S)-(+)-isomer is not only 70% more efficacious but also accumulates much less in ocular tissues than the (R)-(−)-isomer. As such, (S)-(+)-hydroxychloroquine sulfate is more effective and much safer than (±)-hydroxychloroquine sulfate for patients who take long-term medication at high dosages.

In addition, a drug in a crystalline form is more stable and easier to process when used to prepare pharmaceutical compositions.

Thus, there is need for crystals of (S)-(+)-hydroxychloroquine sulfate.

SUMMARY

In one aspect, the present invention covers crystals of (S)-(+)-hydroxychloroquine sulfate.

An exemplary crystal has diffraction peaks at 12.3±0.1°, 13.1±0.1°, 17.9±0.1°, 22.8±0.1°, 23.4±0.1°, 25.1±0.1°, and 26.3±0.1° as 2θ angles in a powder X-ray diffraction ("PXRD") pattern. Optimally, it has additional diffraction peaks at 15.0±0.1°, 19.4±0.1°, 20.0±0.1°, 20.4±0.1°, 22.4±0.1°, and 30.8±0.1°.

Another exemplary crystal has diffraction peaks at 12.8±0.1°, 14.5±0.1°, 16.7±0.1°, 17.6±0.1°, 20.2±0.1°, 21.4±0.1°, 23.8±0.1°, 25.7±0.1°, and 26.0±0.1° as 2θ angles in a PXRD pattern. Optimally, it has additional diffraction peaks at 8.1±0.1°, 8.8±0.1°, 19.0±0.1°, 21.7±0.1°, 22.3±0.1°, 26.7±0.1°, 28.2±0.1°, and 29.3±0.1°.

Also contemplated are crystals each having an endothermic peak at 242.7±0.1° C. or 245.2±0.1° C. in a differential scanning calorimetry curve.

In a second aspect, this invention covers a method of preparing the above-described crystals of (S)-(+)-hydroxychloroquine sulfate. The method includes dissolving a salt-free form of (±)-hydroxychloroquine in a solvent, adding a chiral organic acid to precipitate and obtain a (S)-(+) hydroxychloroquine salt, neutralizing the salt to obtain a salt-free form of (S)-(+) hydroxychloroquine, preparing a salt-free form of (S)-(+) hydroxychloroquine solution, and adding sulfuric acid to precipitate and obtain a crystal of (S)-(+) hydroxychloroquine sulfate. By heating the crystal thus obtained in a solvent at 45° C.-55° C. for 2-4 hours, another crystal of this invention is formed.

The details of embodiments of the invention are set forth in the description below. Other features, objects, and advantages of the invention will be apparent from the figures and from the claims.

BRIEF DESCRIPTION OF THE DRAWINGS

FIG. 1 shows a PXRD pattern of a first crystal of (S)-(+)-hydroxychloroquine sulfate ("type A crystal") as 2θ angles.

FIG. 2 shows a differential scanning calorimetry curve of type A crystal.

FIG. 3 shows a PXRD pattern of a second crystal of (S)-(+)-hydroxychloroquine sulfate ("type B crystal") as 2θ angles.

FIG. 4 shows a differential scanning calorimetry curve of type B crystal.

FIG. 5 shows a PXRD pattern of a third crystal of (S)-(+)-hydroxychloroquine sulfate ("type C crystal") as 2θ angles.

FIG. 6 shows a PXRD pattern of a fourth crystal of (S)-(+)-hydroxychloroquine sulfate ("type D crystal") as 2θ angles.

FIG. 7 shows a moisture adsorption curve and a moisture desorption curve of type A crystal.

FIG. 8 shows a moisture adsorption curve and a moisture desorption curve of type B crystal.

FIG. 9 shows a moisture adsorption curve and a moisture desorption curve of an amorphous form of (S)-(+)-hydroxychloroquine sulfate.

DETAILED DESCRIPTION

Described in detail below are crystals of (S)-(+)-hydroxychloroquine sulfate and their preparation.

In one embodiment, a crystal of (S)-(+)-hydroxychloroquine sulfate, i.e., type A crystal, features diffraction peaks at 12.3±0.1°, 13.1±0.1°, 15.0±0.1°, 17.9±0.1°, 19.4±0.1°, 20.0±0.1°, 20.4±0.1°, 22.4±0.1°, 22.8±0.1°, 23.4±0.1°, 25.1±0.1°, 26.3±0.1°, and 30.8±0.1° as 2θ angles. See FIG. 1. The crystal further features an endothermic peak at 242.7±0.1° C. in a differential scanning calorimetry curve. See FIG. 2.

In another embodiment, a crystal of (S)-(+)-hydroxychloroquine sulfate, i.e., type B crystal, features diffraction peaks at 8.1±0.1°, 8.8±0.1°, 12.8±0.1°, 14.5±0.1°, 16.7±0.1°, 17.6±0.1°, 19.0±0.1°, 20.2±0.1°, 21.4±0.1°, 21.7±0.1°, 22.3±0.1°, 23.8±0.1°, 25.7±0.1°, 26.0±0.1°, 26.7±0.1°, 28.2±0.1°, and 29.3±0.1° as 2θ angles. See FIG. 3. The crystal further features an endothermic peak at 245.2±0.1° C. in a differential scanning calorimetry curve. See FIG. 4.

Type A crystal is prepared according to the procedure set forth below:

dissolving a salt-free form of (±)-hydroxychloroquine in a first solvent to obtain a first solution, adding into the first solution a second solution that contains a chiral organic acid in a second solvent to obtain a third solution, adding a third solvent to the third solution to precipitate a (S)-(+)-hydroxychloroquine salt, neutralizing the (S)-(+)-hydroxychloroquine salt to obtain a salt-free form of (S)-(+)-hydroxychloroquine, dissolving the salt-free form of (S)-(+)-hydroxychloroquine in a fourth solvent to obtain a fourth solution, and adding into the fourth solution a fifth solution that contains sulfuric acid in a fifth solvent to precipitate and obtain a crystal of (S)-(+)-hydroxychloroquine sulfate, i.e., type A crystal.

A preferred chiral organic acid is a derivative of a chiral tartaric acid, e.g., (+)-dibenzoyl-D-tartaric acid, (+)-di-p-toluene-D-tartaric acid, or (+)-di-p-anisoyl-D-tartaric acid.

Each of the first solvent, the second solvent, and the third solvent is preferably a polar organic solvent or a combination of two or more polar organic solvents, e.g., a combination of dimethyl sulfoxide ("DMSO") and acetonitrile at a 1:1 volume ratio.

Preferably, the fourth solvent is a polar organic solvent and the fifth solvent is a polar organic solvent or water. As examples, the fourth solvent is acetonitrile and the fifth solvent is ethanol.

Another crystal covered by the invention can be prepared by dissolving type A crystal (S)-(+)-hydroxychloroquine sulfate in a sixth solvent and then heating the resulting solution at 45° C.-55° C. for 2-4 hours to precipitate and obtain type B crystal.

Preferably, the sixth solvent is ethanol and the heating temperature is 50° C.

Crystals of (S)-(+)-hydroxychloroquine sulfate can be analyzed by PXRD using Empyrean and X'Pert³ Powder diffractometers from Malvern PaNalytical (Netherland). More specifically, the crystals are scanned from 3° to 40° (2θ) in a continuous mode. The X-ray light source is Cu Kα radiation (Kα1=1.540598 Å, Kα2=1.544426 Å, Kα2/Kα1=0.5).

The crystals can also be analyzed in the heating gradient of 10° C./min using a differential scanning calorimetry ("DSC") 2500 thermal differential analyzer from TA Instruments (USA).

Without further elaboration, it is believed that one skilled in the art can, based on the above description, utilize the present invention to its fullest extent. The following examples are to be construed as merely illustrative and not limitative of the remainder of the disclosure in any way whatsoever.

Example 1: Preparation and Characterization of Type a Crystal of (S)-(+)-Hydroxychloroquine Sulfate Type A crystal of (S)-(+)-hydroxychloroquine sulfate was prepared according to the method described below.

Preparation of a Salt-Free Form of (+)-Hydroxychloroquine Solution 5 g (±)-hydroxychloroquine sulfate was dissolved in 11 mL water at room temperature. To the resulting solution, 25 mL ethyl acetate and 14 mL aqueous sodium hydroxide solution (2M) were added subsequently and the reaction solution was stirred at room temperature for 1 hour. The organic phase was separated from the aqueous phase, dried over sodium sulfate, and concentrated to give an oil. The oil was dissolved in 5 mL acetonitrile. To the solution was added dropwise 45 mL water at room temperature. The resulting solution was stirred at room temperature overnight to form a white precipitate. The precipitate was isolated by centrifugation and dried under vacuum overnight at room temperature to give a salt-free form of (±)-hydroxychloroquine as a white solid.

The salt-free form of (±)-hydroxychloroquine was tested for its solubility in each of 16 solvents (see Table 1 below) by adding to a glass vial containing 2 mg (±)-hydroxychloroquine a solvent in volumes of 50 μL, 50 μL, 200 μL, and 700 μL successively until the white solid was completely dissolved or the solvent volume reached 1 mL.

As shown in Table 1 below, the salt-free form of (±)-hydroxychloroquine was highly soluble in a polar organic solvent, having a solubility parameter over 40 mg/mL. On the other hand, it was poorly soluble in a non-polar solvent and water, having a solubility parameter less than 2.1 mg/mL.

TABLE 1

| Solvent | Solubility (mg/mL) | Solvent | Solubility (mg/mL) |
|---|---|---|---|
| Methanol | >40 | Tetrahydrofuran | >38 |
| Ethanol | >42 | 2-Methyl-tetrahydrofuran | >38 |
| Isopropanol | >38 | Dioxane | >40 |
| Acetone | >38 | Acetonitrile | 6.7-20 |
| Methyl isobutyl ketone | >42 | n-Heptane | <2.1 |
| Ethyl acetate | 6.7-20 | Toluene | <2.0 |
| Isopropyl acetate | 6.7-20 | Water | <1.9 |
| Methyl tert-butyl ether | <2.1 | Dichloromethane | >40 |

Preparation of a Crystal of (S)-(+)-Hydroxychloroquine Salt by Reacting Salt-Free Form of (+)-Hydroxychloroquine with a Chiral Organic Acid To prepare a crystal of (S)-(+)-hydroxychloroquine salt, reactions were carried out by mixing salt-free form of (+)-hydroxychloroquine with a chiral organic acid. Four studies were conducted to optimize the reaction conditions. More specifically, they aimed to identify optimal chiral organic acids, optimal solvents, optimal molar ratios between (±)-hydroxychloroquine and a chiral organic acid, and optimal reaction times/solvent ratios.

Study 1: Identifying Optimal Chiral Organic Acids

An ideal chiral organic acid should meet three criteria: cost-effective, capable of forming a crystal with (±)-hydroxychloroquine, and chirally pure.

Base on the solubility test results shown in Table 1, five solvent systems, each a two-solvent mixture, were used in this study. See Table 2 below. Each of twelve chiral organic acids, listed in Table 2, was screened for in-situ precipitation of a (S)-(+)-hydroxychloroquine salt by dissolving the salt-free form of (±)-hydroxychloroquine in each of the five solvent systems to form a solution at a concentration of 40 mg/mL and then adding an equimolar chiral organic acid, in solid form, to 0.5 mL of the solution. The reaction solution was stirred at room temperature for 2 days.

As shown in Table 2, three tartaric acid derivatives, i.e., dibenzoyl-L-tartaric acid, (−)-di-p-toluene-L-tartaric acid, and (+)-di-p-anisoyl-D-tartaric acid, gave in-situ precipitates, i.e., amorphous salts.

TABLE 2

| chiral acid | THF*/n-Heptane (1:1, v/v) | THF/n-Heptane (9:1, v/v) | Ethanol/n-Heptane (1:1, v/v) | Acetone/n-Heptane (1:1, v/v) | Acetone/n-Heptane (4:1, v/v) |
|---|---|---|---|---|---|
| 1 (+)-3-Bromocamphor-10-sulfonic acid monohydrate | Gel | Clear | Oil | Oil | Oil |
| 2 D-camphorsulfonic acid | Oil | Oil | Oil | Oil | Oil |
| 3 Dibenzoyl-L-tartaric acid | Amorphous | Amorphous | Gel | Amorphous | Amorphous |
| 4 (−)-Di-p-toluoyl-L-tartaric acid | Amorphous | | Gel | Amorphous | |
| 5 D-Tartaric acid | Oil | Gel | Gel | Gel | Gel |
| 6 (+)-Di-p-anisoyl-D-tartaric acid | Amorphous | Amorphous | Amorphous | Amorphous | Gel |
| 7 D-Glucuronic acid | Acid precipitated | | Gel | Acid precipitated | Acid precipitated |
| 8 L-Pyroglutamic acid | Gel | Gel | Oil | Gel | Gel |
| 9 (S)-(+)-Mandelic acid | Oil | Oil | Oil | Oil | Oil |
| 10 D-(+)-Malic acid | Gel | Gel | Oil | Gel | Gel |
| 11 L-Lactic acid | Gel | Gel | Oil | Oil | Clear |
| 12 D-Isoascorbic acid | Gel | Gel | Gel | Gel | Gel |

*THF stands for tetrahydrofuran.

Study 2: Identifying Optimal Solvent Combinations

Combinations of two solvents at different volume ratios were screened for crystallization of hydroxychloroquine dibenzoyl-D-tartaric acid ("DBDT") salt as follows. See Table 3 below. First, the salt-free form of (±)-hydroxychloroquine (80 mg/mL) and an equimolar DBDT were added into each combination. The reaction solution was then stirred at room temperature for 1-2 days and the precipitate thus formed was separated by centrifugation. The supernatant solution was filtered and analyzed. The amounts of (R)-(−) hydroxychloroquine DBDT salt and (S)-(+)-hydroxychloroquine DBDT salt in each supernatant solution were determined by high performance liquid chromatography ("HPLC", 1100/1260 HPLC from Agilent, USA) at a detector wavelength of 254 nm UV.

As shown in Table 3, combinations of DMSO and acetonitrile gave a higher R/S selectivity than combinations of methanol and acetonitrile, indicating a higher S/R selectivity in the precipitate.

TABLE 3

| | Solvents (v/v) | Supernatant solutions | | |
|---|---|---|---|---|
| | | R (mg/mL) | S (mg/mL) | R/S |
| 1 | DMSO/Acetonitrile (1:2) | 5.7 | 0.3 | 17.8 |
| 2 | DMSO/Acetonitrile (1:1.5) | 1.0 | 0.2 | 5.2 |
| 3 | DMSO/Acetonitrile (1:1) | 2.5 | 0.4 | 5.7 |
| 4 | DMSO/Acetonitrile (2:1) | 5.6 | 1.1 | 5.0 |
| 5 | DMSO/Acetonitrile (1:0) | 15.6 | 2.6 | 5.8 |
| 6 | Methanol/Acetonitrile (19:1) | 14.6 | 31.1 | 0.5 |
| 7 | Methanol/Acetonitrile (2:1) | 12.6 | 25.4 | 0.5 |

Study 3: Identifying Optimal Molar Ratios Between (+)-Hydroxychloroquine and a Chiral Organic Acid Six reactions were performed. Referring to Table 4 below, in each reaction, a mixture of (±)-hydroxychloroquine, DBDT, and a catalytic amount of a crystal of (±)-hydroxychloroquine DBDT salt in DMSO was stirred at room temperature for 2 days. The precipitate thus formed was separated by centrifugation. The supernatant solution was filtered and analyzed. The amounts of (R)-(−) hydroxychloroquine DBDT salt and (S)-(+) hydroxychloroquine DBDT salt in the supernatant solution were determined by HPLC as describe above.

As shown in Table 4, an equimolar (±)-hydroxychloroquine/DBDT gave a much higher R/S selectivity than the other molar ratios, indicating a much higher S/R selectivity in the precipitate.

TABLE 4

| | DMSO (ml) | (±)-hydroxychloroquine (mg/ml) | (±)-hydroxychloroquine/DBDT molar ratio | Supernatant solution | | |
|---|---|---|---|---|---|---|
| | | | | R (mg/ml) | S (mg/ml) | R/S |
| 1 | 1.5 | 27.2 | 1:0.5 | 12.3 | 8.1 | 1.5 |
| 2 | 1.5 | 26.6 | 1:0.75 | 10.8 | 2.9 | 3.7 |
| 3 | 1.5 | 26.8 | 1:1.5 | 10.8 | 2.7 | 4.0 |
| 4 | 1.3 | 31.0 | 1:1 | 13.6 | 2.2 | 6.2 |
| 5 | 2.0 | 20.2 | 1:1 | 7.8 | 2.1 | 3.7 |
| 6 | 0.5 | 80.0 | 1:1 | 15.6 | 2.6 | 5.8 |

Study 4: Identifying Optimal Reaction Times/Solvent Ratios

A solution containing 16 g DBDT dissolved in 100 mL DMSO was added dropwise over 4 hours to another solution containing 15.0 g (±)-hydroxychloroquine dissolved in 426 mL DMSO. The reaction solution was stirred at room temperature overnight. Afterwards, 80 mL of the reaction solution was transferred into 10 vials, each vial containing 8 mL solution. The remaining reaction solution was used in the manner as described below to prepare type A crystal of the (S)-(+)-hydroxychloroquine sulfate. To the 10 vials, different amounts of acetonitrile were added. See Table 5 below. The solution in each vial was then stirred at room temperature for different lengths of time. Also see Table 5. A precipitate formed in each reaction solution was separated by centrifugation. Each supernatant solution was filtered and analyzed. The amounts of (R)-(−) hydroxychloroquine DBDT salt and (S)-(+) hydroxychloroquine DBDT salt in the supernatant solution were determined by HPLC as describe above.

As shown in Table 5, the reaction stirred for 2 days in a combination of DMSO and acetonitrile at the 1:1 volume ratio gave the highest R/S selectivity, i.e., 4.8, indicating more (S)-(+) hydroxychloroquine DBDT salt in the precipitate.

TABLE 5

| | DMSO/acetonitrile (v/v) | Stirring time (day) | Supernatant solution | | |
|---|---|---|---|---|---|
| | | | R (mg/mL) | S (mg/mL) | R/S |
| 1 | 4:1 | 0.5 | 8.1 | 4.2 | 1.9 |
| 2 | | 1.0 | 7.0 | 2.5 | 2.8 |
| 3 | | 1.5 | 7.7 | 2.6 | 3.0 |
| 4 | | 3.0 | 7.1 | 2.4 | 3.0 |
| 5 | | 4.0 | 7.6 | 2.2 | 3.5 |
| 6 | 2:1 | 1.0 | 6.7 | 1.8 | 3.7 |
| 7 | | 2.0 | 5.5 | 1.5 | 3.7 |
| 8 | | 3.0 | 6.1 | 1.9 | 3.2 |
| 9 | 1:1 | 0.5 | 3.9 | 1.5 | 2.6 |
| 10 | | 2.0 | 4.3 | 0.9 | 4.8 |

Preparation of Type a Crystal of (S)-(+)-Hydroxychloroquine Sulfate

To a reaction solution obtained from Study 4 (480 mL) was added acetonitrile (480 mL) to give a (S)-(+)-hydroxychloroquine DBDT salt. The salt was washed with DMSO to obtain a crystal of S-hydroxychloroquine DBDT salt (4.4 g, 95% ee). The crystal was neutralized with a base solution and extracted with ethyl acetate/water to obtain a salt-free form of (S)-(+)-hydroxychloroquine (1.8 g). The salt-free form of (S)-(+)-hydroxychloroquine was dissolved in acetonitrile (60 mL). To the resulting solution was added dropwise a solution containing sulfuric acid (25.7 mL) in ethanol (19.5 mL) in 30 minutes. The reaction solution was stirred at 50° C. for 1 hour and then cooled down to room temperature. A solid was formed in the reaction solution. The solid was collected by centrifugation and dried under vacuum at room temperature for 4 hours to obtain 1.7 g of type A crystal of (S)-(+)-hydroxychloroquine sulfate with an ee of 96.2% ("ee" stands for enantiomeric excess).

Characterization of Type a Crystal of (S)-(+)-Hydroxychloroquine Sulfate

Type A crystal of (S)-(+)-hydroxychloroquine sulfate thus obtained was analyzed by PXRD.

As shown in FIG. 1, type A crystal features diffraction peaks at 12.3±0.1°, 13.1±0.1°, 15.0±0.1°, 17.9±0.1°, 19.4±0.1°, 20.0±0.1°, 20.4±0.1°, 22.4±0.1°, 22.8±0.1°, 23.4±0.1°, 25.1±0.1°, 26.3±0.1°, and 30.8±0.1° as 2θ angles in a PXRD pattern.

The crystal was also analyzed by DSC. As shown in FIG. 2, it features an endothermic peak at 242.7±0.1° C. in a DSC curve.

Further, the stability of type A crystal was determined by stirring the crystal (10 mg) in each of nine solvent (0.5 mL) at room temperature for 1 day. For the nine solvents, see Table 6 below. The resulting solid was analyzed by XRPD and chiral HPLC containing a chiral column of DAICEL CHIRALCEL OD-H, 250×4.6 mm, 5 μm.

TABLE 6

| | Solvent | Results of solid analysis | |
|---|---|---|---|
| | | Crystal change | ee (%) |
| 1 | Ethanol | Not found | 96.7 |
| 2 | Methanol | Clear solution | Clear solution |
| 3 | Ethyl acetate | Not found | 88.8 |
| 4 | Isopropyl acetate | Not found | 95.5 |
| 5 | Acetone | Not found | 95.4 |

TABLE 6-continued

| | Solvent | Results of solid analysis | |
|---|---|---|---|
| | | Crystal change | ee (%) |
| 6 | Tetrahydrofuran | Not found | 95.3 |
| 7 | Acetonitrile | Not found | 95.6 |
| 8 | Dichloromethane | Not found | 95.8 |
| 9 | Ethanol/water (9/1) | Not found | 99.2 |

As shown in Table 6, type A crystal was unexpectedly stable in all test solvents except in methanol where the crystal was completely dissolved to form a clear solution. Even more unexpectedly, its ee value in ethanol/water (9/1) increased from 96.2% to 99.2%.

The stability of type A crystal was also determined by heating the crystal to 30° C., 80° C., 130° C., 160° C., 180° C., and 210° C. under nitrogen using the Variable Temperature PXRD technique. Again, it was unexpected that type A crystal was highly stable at room temperature. Only when the temperature reached 80° C., 160° C. and 210° C., it was converted to type B, C, and D crystals, respectively. The PXRD patterns of type B, C, and D crystals are shown in FIG. 3, FIG. 5, and FIG. 6.

Example 2: Preparation and Characterization of Type B Crystal of (S)-(+)-Hydroxychloroquine Sulfate To prepare type B crystal of (S)-(+)-hydroxychloroquine sulfate, type A crystal of (S)-(+)-hydroxychloroquine sulfate (1.5 g) was dissolved in ethanol (5 mL) and then stirred at 50° C. for 4 hours to precipitate and obtain type B crystal of (S)-(+)-hydroxychloroquine sulfate (1.5 g) with an ee of 99%.

Type B crystal was analyzed by PXRD. As shown in FIG. 3, it features diffraction peaks at 8.1±0.1°, 8.8±0.1°, 12.8±0.1°, 14.5±0.1°, 16.7±0.1°, 17.6±0.1°, 19.0±0.1°, 20.2±0.1°, 21.4±0.1°, 21.7±0.1°, 22.3±0.1°, 23.8±0.1°, 25.7±0.1°, 26.0±0.1°, 26.7±0.1°, 28.2±0.1°, and 29.3±0.1° as 2θ angles.

The crystal was also analyzed by DSC. As shown in FIG. 4, it has an endothermic peak at 245.2±0.1° C. in a differential scanning calorimetry curve.

Example 3: Hygroscopicity of Type a Crystal, Type B Crystal, and an Amorphous Form of (S)-(+)-Hydroxychloroquine Sulfate Type A crystal, type B crystal, and an amorphous form of (S)-(+)-hydroxychloroquine sulfate were subjected to dynamic vapor sorption analysis to compare their hygroscopicity using a VTI-SA vapor sorption analyzer from TA Instruments (_New Castle, Del., USA). Each was exposed to a series of relative-humidity ("RH")-change steps at 25° C., i.e, a 5% RH increase per step from 0 to 95% RH and then a 5% RH decrease per step from 95% to 5% RH. Moisture contents for humidity-increasing steps and for humidity-decreasing steps were then recorded to generate, respectively, adsorption curves and desorption curves as shown in FIG. 7, FIG. 8, and FIG. 9.

Referring to the adsorption carves in the figures, (i) type A crystal did not adsorb moisture at RH as high as 85%, type B crystal adsorbed moisture only at RH higher than 60%, and, by contrast, the amorphous form adsorbed moisture at RH as low as 25% and (ii) at 95% RH, the moisture contents of type A crystal, type B crystal, and the amorphous form were 19%, 30%, and 51%, respectively. Further, the desorption curves A these three figures indicate that the amorphous form was much more susceptible to an environment than both type A and type B crystals in view of its much steeper curvature.

The results set forth above, which were unexpected, clearly demonstrate that both type A and type B crystals are less hygroscopic, much more stable, and, thus, much easier to handle than the amorphous form when used to prepare pharmaceutical compositions.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A crystal of (S)-(+)-hydroxychloroquine sulfate, wherein the crystal has diffraction peaks at 12.3±0.1°, 13.1±0.1°, 17.9±0.1°, 22.8±0.1°, 23.4±0.1°, 25.1±0.1°, and 26.3±0.1° as 2θ angles in a powder X-ray diffraction ("PXRD") pattern.

2. The crystal of claim 1, further having diffraction peaks at 15.0±0.1°, 19.4±0.1°, 20.0±0.1°, 20.4±0.1°, 22.4±0.1°, and 30.8±0.1°.

3. The crystal of claim 1, further having an endothermic peak at 242.7±0.1° C. in a differential scanning calorimetry curve.

4. The crystal of claim 2, further having an endothermic peak at 242.7±0.1° C. in a differential scanning calorimetry curve.

5. A crystal of (S)-(+)-hydroxychloroquine sulfate, wherein the crystal has diffraction peaks at 12.8±0.1°, 14.5±0.1°, 16.7±0.1°, 17.6±0.1°, 20.2±0.1°, 21.4±0.1°, 23.8±0.1°, 25.7±0.1°, and 26.0±0.1° as 2θ angles in a PXRD pattern.

6. The crystal of claim 5, further having diffraction peaks at 8.1±0.1°, 8.8±0.1°, 19.0±0.1°, 21.7±0.1°, 22.3±0.1°, 26.7±0.1°, 28.2±0.1°, and 29.3±0.1°.

7. The crystal of claim 5, further having an endothermic peak at 245.2±0.1° C. in a differential scanning calorimetry curve.

8. The crystal of claim 6, further having an endothermic peak at 245.2±0.1° C. in a differential scanning calorimetry curve.

9. A method of preparing a crystal of (S)-(+)-hydroxychloroquine sulfate of claim 1 comprising:

dissolving a salt-free form of (±)-hydroxychloroquine in a first solvent to obtain a first solution, adding into the first solution a second solution that contains a chiral organic acid in a second solvent to obtain a third solution, adding a third solvent to the third solution to precipitate a (S)-(+)-hydroxychloroquine salt, neutralizing the (S)-(+)-hydroxychloroquine salt to obtain a salt-free form of (S)-(+)-hydroxychloroquine, dissolving the salt-free form of (S)-(+)-hydroxychloroquine in a fourth solvent to obtain a fourth solution, and adding into the fourth solution a fifth solution that contains sulfuric acid in a fifth solvent to precipitate and obtain a crystal of (S)-(+)-hydroxychloroquine sulfate of claim 1 having an endothermic peak at 242.7±0.1° C. in a differential scanning calorimetry curve.

10. The method of claim 9, wherein the chiral organic acid is a derivative of a chiral tartaric acid.

11. The method of claim 10, wherein the chiral organic acid is (+)-dibenzoyl-D-tartaric acid, (+)-di-p-toluene-D-tartaric acid, or (+)-di-p-anisoyl-D-tartaric acid.

12. The method of claim 9, wherein each of the first solvent, the second solvent, and the third solvent is a polar organic solvent or a combination of two or more polar organic solvents.

13. The method of claim 12, wherein each of the first solvent, the second solvent, and the third solvent is a combination of dimethyl sulfoxide and acetonitrile at a 1:1 volume ratio.

14. The method of claim 9, wherein the fourth solvent is a polar organic solvent and the fifth solvent is a polar organic solvent or water.

15. The method of claim 14, wherein the fourth solvent is acetonitrile and the fifth solvent is ethanol.

16. A method of preparing a crystal of (S)-(+)-hydroxychloroquine sulfate of claim 5 comprising:

dissolving a salt-free form of (±)-hydroxychloroquine in a first solvent to obtain a first solution, adding into the first solution a second solution that contains a chiral organic acid in a second solvent to obtain a third solution, adding a third solvent to the third solution to precipitate a (S)-(+)-hydroxychloroquine salt, neutralizing the (S)-(+)-hydroxychloroquine salt to obtain a salt-free form of (S)-(+)-hydroxychloroquine, dissolving the salt-free form of (S)-(+)-hydroxychloroquine in a fourth solvent to obtain a fourth solution, and adding into the fourth solution a fifth solution that contains sulfuric acid in a fifth solvent to precipitate and obtain a crystal of (S)-(+)-hydroxychloroquine sulfate of claim 1 having an endothermic peak at 242.7±0.1° C. in a differential scanning calorimetry curve, dissolving the crystal of (S)-(+)-hydroxychloroquine sulfate of claim 1 in a sixth solvent, and heating the resulting solution at 45° C.-55° C. for 2-6 hours or longer to precipitate and obtain a crystal of (S)-(+)-hydroxychloroquine sulfate of claim 5 having an endothermic peak at 245.2±0.1° C. in a differential scanning calorimetry curve.

17. The method of claim 16, wherein the sixth solvent is ethanol.

18. The method of claim 16, wherein the resulting solution is heated at 50° C.

* * * * *